Figure 1:
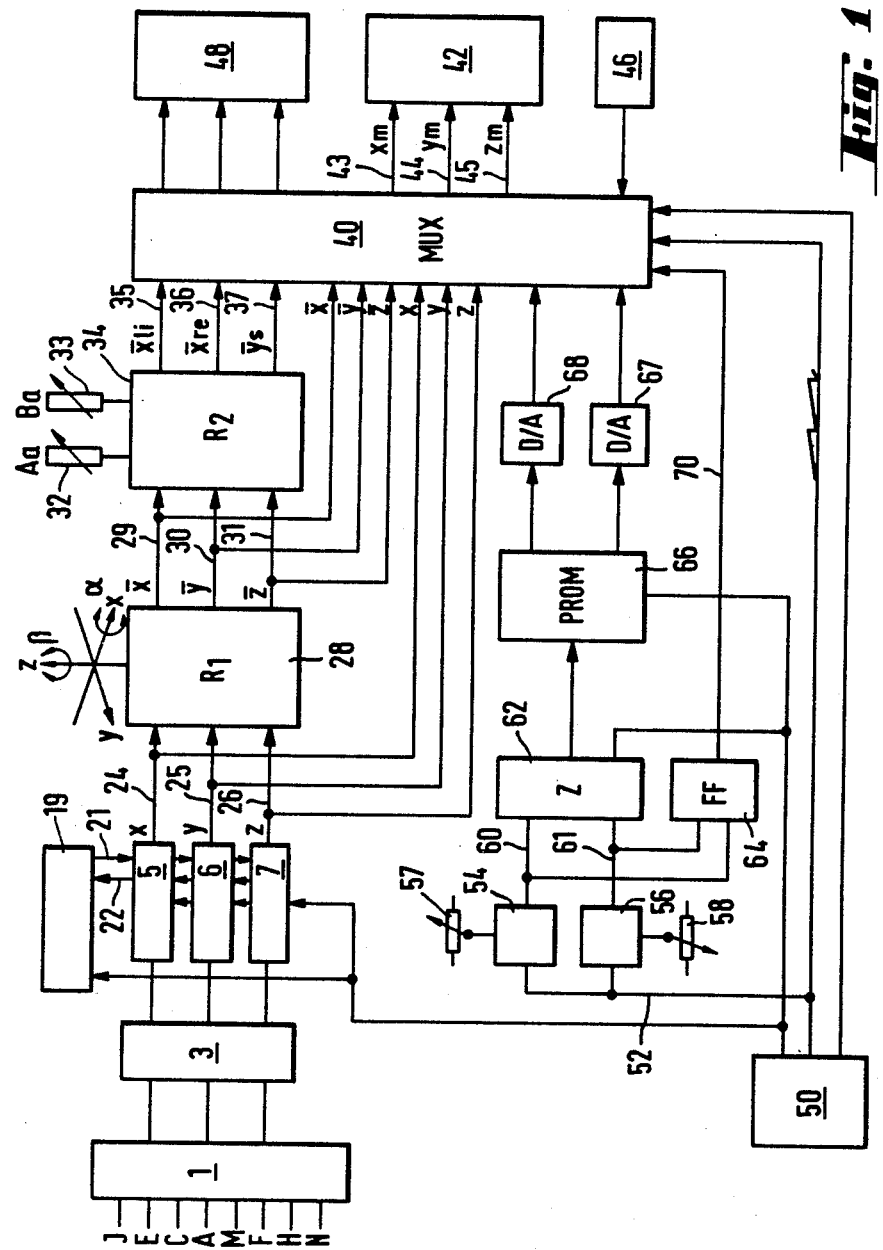

United States Patent [19]
Krause et al.

[11] 4,292,977
[45] Oct. 6, 1981

[54] METHOD AND DEVICE FOR REPRESENTING ELECTRICAL SPATIAL LINES AND SPATIAL IMAGES

[75] Inventors: Heinz Krause; Bert Sanner, both of Freiburg, Fed. Rep. of Germany

[73] Assignee: J. F. Tönnies Erben K.G., Freiburg im Breisgau, Fed. Rep. of Germany

[21] Appl. No.: 37,119

[22] Filed: May 8, 1979

[30] Foreign Application Priority Data

May 8, 1978 [DE] Fed. Rep. of Germany ....... 2819999
Mar. 2, 1979 [DE] Fed. Rep. of Germany ....... 2908424

[51] Int. Cl.³ ............................................. A61B 5/04
[52] U.S. Cl. ..................................... 128/712; 128/653; 128/660
[58] Field of Search .......................... 128/699, 710–712, 128/660–661, 653; 73/602; 364/414–415, 417, 515, 518, 521–522, 731, 815; 367/7, 11

[56] References Cited

U.S. PATENT DOCUMENTS

| | | | |
|---|---|---|---|
| 3,186,403 | 6/1965 | Bassett | 128/699 |
| 3,671,730 | 6/1972 | Pilato | 364/815 |
| 3,884,221 | 5/1975 | Eastman | 128/699 |
| 4,086,492 | 4/1978 | Lodge et al. | 250/445 T |
| 4,100,916 | 7/1978 | King | 128/661 |
| 4,141,347 | 2/1979 | Green et al. | 128/663 |

FOREIGN PATENT DOCUMENTS

| | | | |
|---|---|---|---|
| 2804732 | 8/1978 | Fed. Rep. of Germany | 128/653 |
| 2354598 | 2/1978 | France | 364/522 |

OTHER PUBLICATIONS

Silcocks, H. et al., "Various Methods of Displaying Computer–Generated 3–D VCG's", Proc. 7th Ann. Biol. Sci. Instr. Symp., Ann Arbor, Mich. May 1969, pp. 37–43.

Plott; H. H. et al., "A Real Time Stereoscopic Small Computer Graphics Display System", IEEE Trans. on Systems, Man & Cyber. vol. 5, No. 5 Sep. 1975, pp. 527–533.

Moritz, W. E. et al., "A uP–Based Spatial Locating System for Use with Diag. UTS", IEEE Proc. vol. 64, No. 6, pp. 966–974, Jun. 1976.

Katz, G. et al., "Capturing the Third Dimension", Computer Decisions, Oct. 1970, pp. 50–53.

*Primary Examiner*—Robert W. Michell
*Assistant Examiner*—Francis J. Jaworski
*Attorney, Agent, or Firm*—Herbert L. Lerner

[57] ABSTRACT

Method and device for representing electrical spatial curves and spatial images of electrically reproduced ultrasonic images, X-ray images or cardiac vector loops, which includes separately storing in an electronic memory coordinates of action currents occurring in time for the spatial curves of images to be represented, calculating transformed coordinates of the spatial curves or images of the action currents in a computer after tilting and rotating by desired angles, two-dimensionally displaying the transformed coordinates on an oscilloscope screen, and viewing three-dimensionally through the tilting and rotating.

3 Claims, 6 Drawing Figures

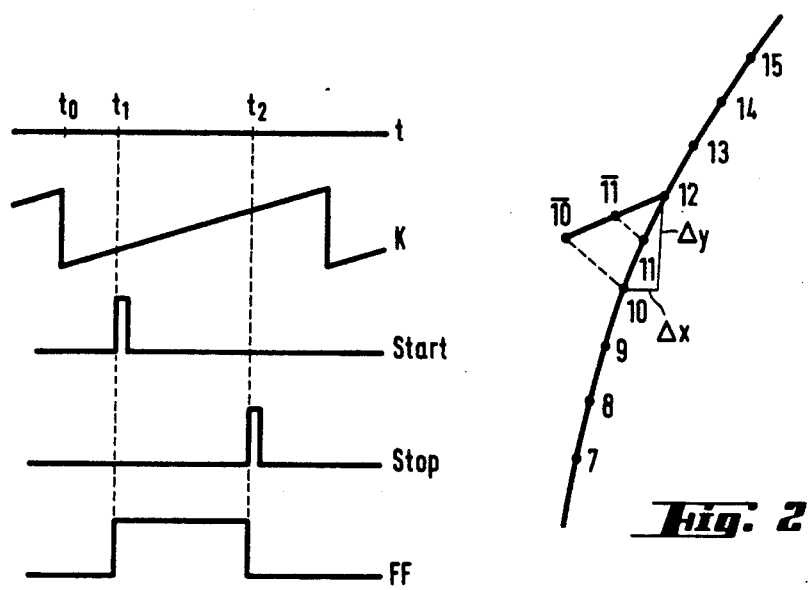
Fig. 2
Fig. 3
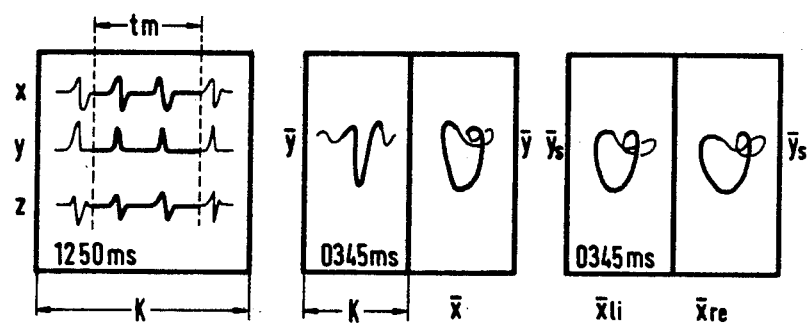
Fig. 4    Fig. 5    Fig. 6

METHOD AND DEVICE FOR REPRESENTING ELECTRICAL SPATIAL LINES AND SPATIAL IMAGES

The invention relates to a method and an arrangement for representing electrical spatial curves and spatial images, especially of electrically reproduced ultrasonic images, X-ray images or of vector loops customary in cardiology.

It is known, for instance, from cardiology, to display the heart action currents of a test person between two respective electrodes separately and to develop from the three customary projections of the three-dimensional curve (frontal, sagittal and horizontal) a concept regarding the three dimensional shape of the curve. The abilities of persons who evaluate the different projections, to perceive the spatial shape of the curves from the individual projections vary greatly, as the visualization is rather limited.

It is therefore an object of the invention to demonstrate the shape of three-dimensional curves, be it from ultrasonic imaging, X-ray images or vector loops in cardiology, in a completely clear and easy-to-visualize manner and to optically display the three-dimensional curves from all sides and from any direction, to record them and to measure them electronically.

The stated problem is solved by the method according to the invention by the provision that coordinates of the action currents occurring in time in the x, y and z direction are kept available separately in an electronic memory; that in a first computer, transformed $\bar{x}$-, $\bar{y}$- and $\bar{z}$- coordinates of the spatial curve or the spatial image tilted by any desired angle $\alpha$ and rotated by any desired angle $\beta$ are calculated, and the transformed coordinates $\bar{x}$, $\bar{y}$ and $\bar{z}$ are displayed two-dimensionally on the picture screen of an oscilloscope; and a three-dimensional visualization is obtained by tilting and rotating.

According to one advantageous embodiment of the invention, the coordinates x, y and z are fed to a second computer for calculating the coordinates of the central projections of the transformed three-dimensional curve or the three-dimensional image from two viewing points, in order to display these central projections for each viewing point separately in two pictures on a picture screen, which are perceived as three-dimensional by means of an optical system. It is a particular advantage that the spatial curves and spatial images can be moved manually by separate adjustment of the angles $\alpha$ and $\beta$ and can be viewed from any side desired.

To mark the course in time and the direction of traversal of the three-dimensional curve, time markers are inserted in the form of lateral jags pointing in arrow fashion in the direction of traversal, the size of the jags depending on the curve velocity.

It has been found to be particularly practical to select any portion of the three-dimensional curve for viewing by selectively using a brightening circuit for measuring the spatial curve or parts thereof timewise, and to indicate the time interval of the brightening digitally. The invention facilitates in an outstanding manner the rapid evaluation of the shape and the velocity of complicated three-dimensional curves and is applicable in particular in electrocardioscopy, where it facilitates and speeds up the diagnostic evaluation of electrocardiograms.

The invention will now be explained in detail by the example of an embodiment for displaying diversions of electrical action currents customary in cardiology (vector loops), where FIG. 1 shows a block diagram of the stereokinetic vector cardioscope, FIG. 2, details of time marking, FIG. 3, a pulse diagram and FIGS. 4 to 6 show screen pictures.

Bioelectric signals of the heart activity are taken from a test person in a manner known per se by means of electrodes placed on the skin, for instance, by means of the Frank network 1 and are fed to a preamplifier 3 which amplifies the signals to a suitable magnitude, for instance, ±5 V. At the output of the preamplifier 3, the coordinates of the integral vector loop are available with their waveform separated by x-, y- and z- direction, and are stored in real time in an electronic memory 5, 6, 7.

To the memories 5, 6, 7 is connected recording equipment 19, for instance, magnetic tape equipment or a perforated-tape punch for documentation, so that the recorded x-, y- and z coordinates can be put in memory again at any time for further analysis. The arrows 21 and 22 shown in the figure from memory 5 for the x-coordinates to the recording equipment 19 indicate the connection between the memory and the recording equipment; the memories 6 and 7 for the y- and z- coordinates are connected to the recording equipment in a similar manner.

The x-, y- and z-coordinates of the memories 5, 6, 7 are fed via lines 24, 25, 26 to a first computer 28. The wave shapes of these x-, y- and z-coordinates describe a curve in space. The three customary projections of this curve (frontal=x/y-projections; sagittal=y/z-projection; horizontal=x/z-projection) define the course in space. To be able to view the course in space more clearly from any direction, the first computer 28 is suitable for calculating the parallel projection of the three-dimensional curve defined by x=f(t), y=f(t) and z=f(t) with its coordinates $\bar{x}$, $\bar{y}$ and $\bar{z}$ transformed by means of tilting by any desired angle $\alpha$ and rotation by any desired angle $\beta$. The result of these transformed coordinates is fed via the lines 29 to 31, the multiplexer 40 and the lines 43 to 45 to the oscilloscope 42 and can be followed up immediately on the picture screen. The angles $\alpha$ and $\beta$ can be set into the first computer 28 (for parallel projection) very plainly by a control stick which can be tilted ($\alpha$) forward and backward and vice-versa and rotated ($\beta$) about its axis in both directions. The manual movement of the control stick together with the visual observation of the picture screen facilitates the spatial perception of the three-dimensional curve or the three-dimensional image considerably.

Since the three-dimensional curve of a cardiological vector loop is actually located in the thorax of a test person, the handle of the control stick is made in the shape of a small bust for correlation reasons. The view of the bust in the tilted and rotated condition corresponds to the view of the spatial curve on the picture screen in the same condition. The frontal, sagittal and horizontal projections can be felt by detents in the control stick.

For stereokinetic observation of the three-dimensional curve or image, a second computer 34 (for central projection) is provided, to which the transformed coordinates $\bar{x}$, $\bar{y}$ and $\bar{z}$ are fed via the lines 29 to 31. The output lines 35 to 37 of the second computer are likewise connected to the multiplexer 40. This second computer 34 permits calculating the coordinates for central projection of the three-dimensionally moving system from two viewing points. The eye distance Aa and the viewing distance Ba can be set by two setting elements 32, 33. The second computer determines the coordinates $\bar{x}li$, $\bar{x}re$ and $\bar{y}$, which serve for the display of two separate images $\bar{x}li/\bar{y}$ and $\bar{x}re/\bar{y}$ on the picture screen of the oscilloscope (FIG. 6). These two images are viewed through a stereo-optical system, inasmuch as the left image ($\bar{x}li/\bar{y}$) is seen by the left eye of the observer and the right image ($\bar{x}re/\bar{y}$) by the right eye of the observer, to whom the curve then appears as three-dimensional.

Through the multiplexer 40 and an operating switch 46 connected thereto, the coordinates x, y and z are switched to the oscilloscope 42 in scalar form, the coordinates $\bar{x}$, $\bar{y}$ and $\bar{z}$ in orthogonal form or the coordinates $\bar{x}li$, $\bar{x}re$ and $\bar{y}$ for a stereo display selectably.

For direct recording of the coordinates, an x-y recorder 48 is provided. The pictures $\bar{x}li/\bar{y}$ and $\bar{x}re/\bar{y}$ can also be written on top of each other by the x-y recorder on paper with green and red ink, respectively. Viewing through glasses of complementary color then also permits one to see the paper image three-dimensionally (anaglyphics method), if the x-, y-, z-system was rotated or tilted as desired.

The following requirements exist for projecting the three-dimensional curve into the two-dimensional paper plane:
1. marking the course in time (time marker) and
2. recognition of the direction in which the curve is traversed.

Since the curve train is called up from the memory 5, 6, 7 and since the memory can also be read out backward in time, the following time and direction markers were applied:

It is assumed that a curve (FIG. 2) runs continuously from 7 to 15 (called up from the memory for instance, by x and y). However, the sequence is written 7 . . . 12, $\overline{11}$, $\overline{10}$, $\overline{11}$, 12 . . . 15. The jag 12, $\overline{10}$, 12 then shows the direction of the curve, and it is repeated in the rhythm of the desired time marker elsewhere (for instance at 22, 32, 42 . . . ).

This course is realized in accordance with the mathematical specification for the coordinates, for instance, of point $\overline{10}$. The coordinates are:

$$x_{12} \pm \Delta y; y_{12} \pm \Delta x.$$

The upper sign applies to jags on the port side of the curve and the lower sign to jags on the starboard side.

The properties of these time markers are:
1. Edge of the curve smooth on one side, no interruption of the curve train.
2. The time markers correspond as to size automatically to the size of the written loops:
   A large loop means high velocity, large $\Delta x$ and $\Delta y$ and thereby, a large jag.
   A small loop means low velocity, small $\Delta x$ and $\Delta y$ and thereby, a small jag.

Electronically, this realization is accomplished in analog technique, using a sample-and-hold circuit. By the example of the jag above, the cycle is as follows:

| Point | Address Counter in SP | Sample/hold | x, | y |
|---|---|---|---|---|
| 10 | up | sample | 0 | |
| 11 | up | sample | 0 | |

| Point | Address Counter in SP | Sample/hold | x, | y |
|---|---|---|---|---|
| 12 | up | hold | 0 | |
| $\overline{11}$ | down | hold | | become larger |
| $\overline{10}$ | down | hold | | |
| $\overline{11}$ | up | hold | | become smaller |
| 12 | up | sample | | |
| 13 | up | sample | 0 | |
| 14 | up | sample | 0 | |

The x, y are added or subtracted as the difference of the values $x_{12}$ hold, $y_{12}$ hold to the respective actual values of x, y.

In the evaluation of the three-dimensional curve on the picture screen either in parallel projection or in central projection, the measurement of the curve as to time is accomplished by a brightening circuit. A control circuit 50 contains a clock generator, a sweep generator and a circuit for flyback blanking. To the sweep output of the control circuit 50 is connected via a line 52 a Schmitt trigger to each monostable multivibrator 54 and 56, by which the beginning and the end of the brightening, i.e., the beginning and the end of the time measurement are fixed. The desired instances for the time measurement can be set at a "start" and a "stop" potentiometer 57 and 58. The outputs of the Schmitt triggers 54 and 56 are connected via lines 60, 61 to start and stop imputs of a counter 62 as well as to "on" and "off" inputs of a bistable multivibrator 64. If, for instance, the counter 62 counts with a frequency of 1000 Hz, the counter reading always gives the result of the time measurement in msec. The counter content is presented by means of a programmable memory 66 (PROM) via digital-to-analog converters 67 and 68 to the multiplexer 40 which continuously interrogates the result and displays it on the oscilloscope 42. The bistable multivibrator 64 is connected via the line 70 to the multiplexer 40 and initiates with its "on" state the brightness control of the monitor.

FIG. 3 illustrates the control of the trigger 54 and 56 and of the bistable multivibrator 64. The instant $t_1$ of the time axis t is determined by the position of the "start" potentiometer 57. At every time $t_1$, as measured from the start of the sweep voltage K, the short start pulse of the start trigger 54 appears, which transfers the bistable multivibrator FF 64 into the "on" state. At the same time, the brightness of the cathode ray beam is turned up and the counter 62 started. At the time $t_2$, which is determined by the "stop" potentiometer 58, there appears at the output of the stop trigger 56 the short stop pulse, which immediately switches the bistable multivibrator FF 64 into the "off" state, whereby the counter 62 is stopped and the cathode ray beam of the monitor is darkened. At the same time, the counting result is indicated at the monitor. FIG. 4 shows a screen picture with the components x, y and z in scalar presentation. The range $t_{mess}$, marked by dashed lines at the sides, is brightened, while the adjoining zones are darkened. The darkening need not be complete; it may be advantageous to show these portions with a dim, just visible brightness. By shifting the limits of the bright section, the time values can now be determined for each section of the curves; they are indicated at the lower edge of the picture screen.

In FIG. 5, the projection plane $\bar{x}/\bar{y}$ is shown in orthogonal presentation on the right half of the screen picture, while on the left half, the curve train for the component $\bar{y}$ is depicted simultaneously in scalar form. The duration of the brightened section of the curve is indicated at the lower edge of the picture screen.

FIG. 6 shows an example for the display for stereoscopic viewing. On the left half of the picture screen the projection $\bar{x}li/\bar{y}$ for the left eye is imaged and to the right, the projection $\bar{x}re/\bar{y}$ for the right eye. The duration of the brightened section is likewise indicated.

We claim:

1. Method for representing electrical spatial curves and spatial images of electrically reproduced ultrasonic images, X-ray images or cardiac vector loops to a stationary viewer on a fixed screen, which comprises separately storing in an electronic memory amperage value coordinates occurring in time for the spatial curves or images to be represented, calculating transformed coordinates of the spatial curves or images of the amperage values in a computer after tilting and rotating relative to the earth by desired angles, two-dimensionally displaying a line from the transformed coordinates on an oscilloscope screen, viewing three-dimensionally through the tilting and rotating relative to the earth, inserting time markers in the form of arrow-shaped lateral jags pointing in the traverse direction of the spatial curves for marking the course in time and direction of traversal of the spatial curves, and determining the size of the jags in dependence on the velocity of the curves.

2. Device for carrying out a method for representing electrical spatial curves and spatial images of electrically reproduced ultrasonic images, X-ray images or cardiac vector loops to a stationary viewer on a fixed screen, comprising sensing means adapted to be coupled to the skin of a test person or on a measurement object for receiving coordinate signals therefrom, a preamplifier connected to said electrodes for receiving said coordinate signals, a memory connected to said preamplifier for storing said coordinate signals, a computer connected to said memory for receiving said cordinate signals and determining transformed coordinates for the spatial curves, means for tilting and rotating said spatial curve transformed coordinates by given angles relative to the earth, means for selectively displaying projections of the spatial curves in a plurality of planes on an oscilloscope screen, a start pulse and a stop pulse circuit, means for controlling said start and stop pulse circuits with a sweep voltage, a counter having a start and stop input connected to said start and stop pulse circuits, respectively, a memory connected to an output of said counter, a multiplexer connected to said memory and to said oscilloscope screen for displaying a reading from said counter thereon, a bistable multivibrator having on and off inputs connected to said start and stop pulse circuits, and a controllable brightening circuit for said oscilloscope screen, said bistable multivibrator having an output connected to said controllable brightening circuit.

3. Device according to claim 2, including a potentiometer connected to each of said pulse circuits for selectively beginning and ending activation of said brightening circuit.

* * * * *